United States Patent [19]

Luttrell

[11] Patent Number: 5,730,597

[45] Date of Patent: Mar. 24, 1998

[54] LIP AND CHEEK RETRACTOR

[75] Inventor: Clifford D. Luttrell, Chesapeake, Va.

[73] Assignee: The United States of America as represented by the Secretary of the Navy, Washington, D.C.

[21] Appl. No.: 658,780

[22] Filed: Jun. 5, 1996

[51] Int. Cl.[6] .................................................. A61C 5/00
[52] U.S. Cl. ........................ 433/140; 600/237; 600/240
[58] Field of Search ............................... 600/237, 238, 600/239, 242; 433/140

[56] References Cited

U.S. PATENT DOCUMENTS

| | | | |
|---|---|---|---|
| 278,520 | 5/1883 | Doyle | 600/242 |
| 548,817 | 10/1895 | Platt | 433/140 |
| 730,184 | 6/1903 | Witter | 433/140 |
| 744,204 | 11/1903 | Jordan . | |
| 1,959,508 | 5/1934 | Sweet | 600/237 X |
| 2,125,980 | 8/1938 | Basil | 433/140 |

*Primary Examiner*—Nicholas D. Lucchesi
*Attorney, Agent, or Firm*—Howard Kaiser

[57] ABSTRACT

A tripartite dental instrument includes a curved-trough-like lip retractor, a flat-fin-like cheek retractor and a straight handle. The handle and the cheek retractor are separately connected to the lip retractor at nearby locations and are each obliquely oriented with respect to the lip retractor. The dental practitioner selectively retracts the patient's lip (upper or lower) and/or cheek (left or right) while the lip retractor cradles the patient's lip at one side of the patient's mouth. The angularities and configurations featured by the inventive dental instrument advantageously afford the dental practitioner unobstructive, noninjurious and precise manipulative adjustability of either or both the lip retraction and cheek retraction functions.

20 Claims, 7 Drawing Sheets

LIP AND CHEEK RETRACTOR

The invention described herein may be manufactured and used by or for the Government of the United States of America for governmental purposes without the payment of any royalties thereon or therefor.

BACKGROUND OF THE INVENTION

The present invention relates to dental devices, more particularly to dental devices used for retracting one or more areas in the vicinity of a patient's mouth for purposes of facilitating oral surgery or other intraoral procedures.

During the performance of a maxillofacial surgical procedure, such as a "Le Fort I osteotomy," simultaneous maximum retraction of both the lip and the cheek is necessary to allow access to soft and hard tissues. Conventional retraction instruments which are currently available permit individual retraction of a lip or a cheek but do not permit simultaneous retraction of both lip and cheek. As a result, the lip tends to droop into the operative field when the cheek retractor is in place, and vice versa.

Another problem with currently available retractors pertains to the standardized right (90 degree) angle of the handle with respect to the working portion. Because of the 90 degree angle, the handle often must be held up within the critically limited peri-oral working area.

Moreover, currently available retractors sometimes perform unsatisfactorily because of the prolonged nature of the typical maxillofacial surgery case. Due to operator and assistant fatigue during long surgeries, the patient's lip is often pinched at the area of exit of the retractor out of the mouth. At times when the retractor is not actively retracting but is passively resting in the mouth, tension on the tissues is released and can result in pressure on the lip.

Recently observed is Jordan's "dental lip and cheek supporter" at U.S. Pat. No. 744,204. Jordan discloses a device which spans the patient's face so as to engage the entire upper lip or lower lip of the patient. At either or both ends of Jordan's device, a prong engages a cheek of the patient. Jordan's device is secured to the patient's head by means of a strap which wraps around the back of the patient's head.

The retraction device according to the present invention was conceived by the inventor prior to his cognizance of the Jordan reference. Jordans's device is not known to be used in any standard dental practice and is not believed to be embraced by conventional dentistry in any aspect thereof.

Indeed, Jordan's device would be impractical or inexpedient in many aspects of dentistry or oral surgery. For example, patients undergoing oral or maxillofacial surgery in the operating room generally require full drapes, with visible isolation effected only of the mouth and nose areas; utilization of Jordan's strap would not be feasible in this context.

Moreover, Jordan's device does not give the impression of being comfortable for the patient. It would seem, for example, that prolonged "Joker-like" contortion of the patient's upper lip may eventually grow tiresome and troublesome for the patient.

In addition, Jordan's device is designed to be strapped firmly in place, thus functioning more like a vice than a maneuverable surgical instrument. Furthermore, Jordan's device tends to pull the patient's tissues to both sides of the patient's face, thereby limiting the amount of distention possible on either side.

SUMMARY OF THE INVENTION

In view of the foregoing, it is an object of the present invention to provide a device which serves to retract both lip and cheek simultaneously.

It is a further object of the present invention to provide such a device which permits dexterous retraction of either the lip or the cheek, or of both lip and cheek to selected respective extents, so as to expose the area or areas of the patient's mouth which require access or visualization.

A further object of this invention is to provide such a device which is designed to work on one side of the the patient's mouth at a time.

Another object of the present invention to provide such a device wherein the handle of the retractor does not obstruct the peri-oral working area.

A further object of this invention is to provide such a device which minimizes injury or discomfort to the patient due to pressure of the device upon the patient's tissues.

These and other objects are accomplished in accordance with the present invention by a dental device which comprises a substantially straight body, a substantially furrowed arm and a substantially flat finger. The substantially furrowed arm branches off the body, from an end of the body, at an acute orientation with respect to the body in each of two perpendicular directions. The substantially flat finger branches off the arm, from a location of the arm which is near the end of the body, at an acute orientation with respect to the body and an obtuse orientation with respect to the arm.

The retraction device according to the present invention comprises a single unit which has three main components, viz., a handle component, a lip retraction component and a cheek retraction component. The inventive retraction device permits delicate maneuvering of the device by the dental (including surgical) practitioner upon one side of the mouth at a time, thereby permitting optimal effectiveness of the device for purposes of exposing or accessing one or more specific areas of the mouth.

Accordingly, the present invention provides a dental instrument which comprises a substantially curvilinearly-channeled structure for retracting a lip, a substantially flat structure for retracting a cheek, and a substantially linear structure for manipulating the instrument. The substantially curvilinearly-channeled structure is connected to the substantially flat structure and the substantially straight structure at proximate locations. The substantially curvilinearly-channeled structure and the substantially flat structure approximately define intersecting axes which form an obtuse angle. The substantially curvilinearly-channeled structure and the substantially linear structure approximately define intersecting axes which form an acute angle in each of two perpendicular directions.

The handle portion and the cheek retraction portion are each obliquely oriented with respect to the lip retraction portion. Advantageously, (a) the cheek retraction portion projects from a location of the lip retraction portion at an obtuse angle with respect to the lip retraction portion, and (b) the handle portion projects from a propinquitous location of the lip retraction portion at an acute angle with respect to the lip retraction portion in each of two perpendicular directions, viz.: (i) in a first direction, the handle portion acutely angled with respect to the imaginary through plane defined by the lip retraction portion; and, (ii) in a second direction, the handle portion acutely angled with respect to the imaginary plane which is axially normal to the imaginary through plane defined by the lip retraction portion.

Other objects, features and advantages of this invention will become apparent from the following detailed description of the invention when considered in conjunction with the accompanying drawings.

BRIEF DESCRIPTION OF THE DRAWINGS

In order that the present invention may be clearly understood, it will now be described, byway of example, with reference to the accompanying drawing, wherein like numbers indicate the same or similar components, and wherein.

DETAILED DESCRIPTION OF THE INVENTION

Figure 1:
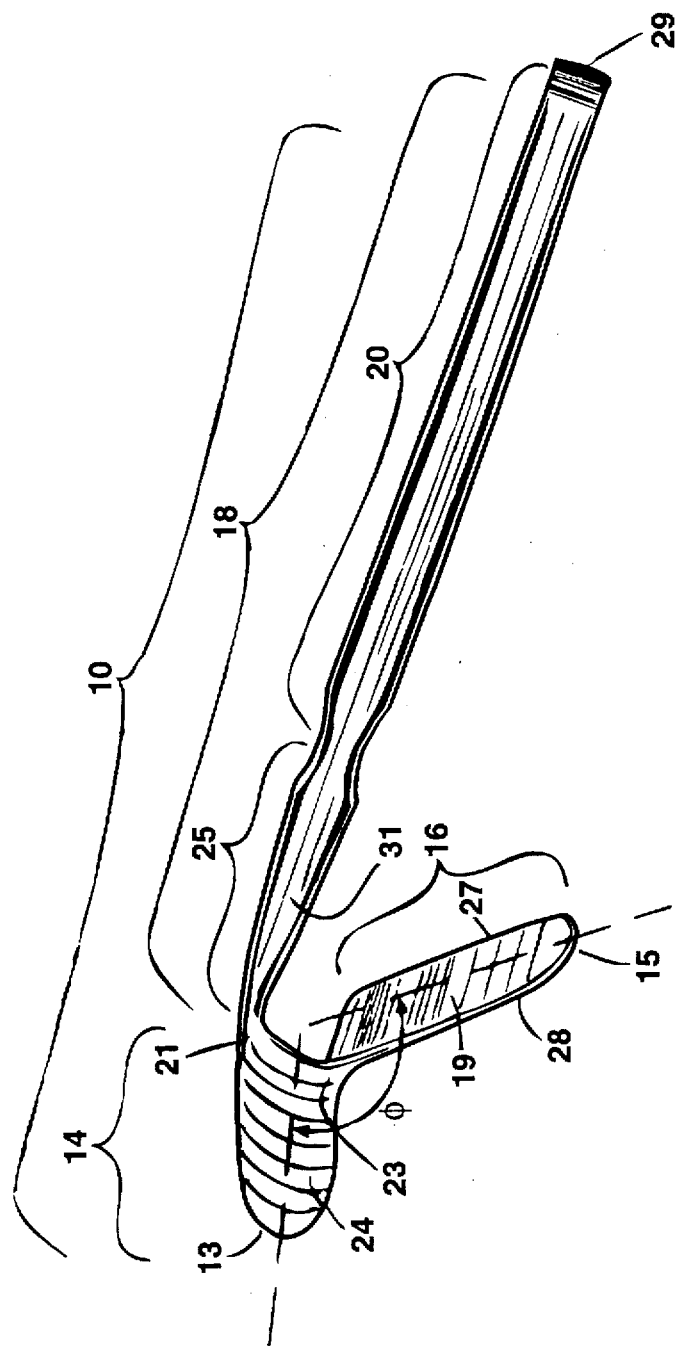
FIG. 1 is a perspective view of an embodiment of the inventive lip and cheek retractor, this embodiment intended for use in the upper left quadrant or lower right quadrant of a patient's mouth.

Referring now to FIG. 1 through FIG. 4, retractor 10 is a preferred embodiment of the retractor in accordance with the present invention. Retractor 10 comprises lip retraction portion 14, cheek retraction portion 16 and handle portion 18. Retractor 10 thus comprises three distinct segments, as distinguished from most currently available retractors, which comprise two distinct segments.

For many embodiments the retractor according to this invention is preferably made of one solid piece of surgical grade steel. Surgical steel would be completely sterilizable for use in the operating room setting where sterility of all instruments is mandatory.

Alternatively, the inventive retractor may be made of a solid steel piece which is coated with a resiliant material (e.g., rubber or plastic); the non-metallic coating would provide more comfortable contact for the patient than would cold hard steel and should be capable of withstanding conventional heat sterilization (e.g., by means of autoclave).

As another alternative, similar advantage in terms of affording superior patient comfort may derive from fabrication of the inventive retractor entirely of a non-metallic material (e.g., plastic, rubber or composite material) which is appropriately robust, resiliant and durable, and which can be subjected to conventional heat sterilization technique while exhibiting dimensional stability; a good candidate for such a material would be a composite molding compound, such as a fiber-filled high temperature thermoplastic resin.

For some embodiments of the present invention, the lip retractor and the cheek retractor form one solid piece and the handle forms a separate solid piece. For such embodiments, the handle piece and the retraction piece may be screwed/unscrewed or otherwise detachably attached. The handle piece and the retraction piece may be made of identical or different materials. For example, it may be economical for the handle piece to be made of surgical steel while the retraction piece is made of a plastic, rubber or composite material. After a dental procedure, the handle piece may be resterilized while the retraction piece may be removed and disposed of. The newly sterile handle piece and a newly replaced sterile retraction piece may be used for the next procedure.

Lip retraction portion 14 includes a curved trough shape having concave side 22 and convex side 24. Lip retraction portion 14 is thus curvilinearly channeled whereby concave side 22 cradles the lip of the patient whether the retractor is at rest or actively retracting the lip. Within its axial plane, lip retraction portion 14 is rounded at its extremity 13.

For most embodiments it is preferable that lip retraction portion 14 have modest convexity-concavity in the lateral direction within its axial plane. Although not readily appreciable in the figures, lip retraction portion 14 is perhaps best shown in FIG. 1 to gently but discernibly curve medially in conformity with the arch shape of the anterior teeth, as manifested by slight curvature of lip retraction portion 14's outer edge 12 and especially of lip retraction portion 14's inner edge 11. Inner edge 11 gradually curves, with increasingly pronounced curvature, into vestibular edge 27 of cheek retraction portion 16.

Cheek retraction portion 16 shown in FIG. 1 through FIG. 4 includes an approximately flat structure which is rounded at its extremity 15 and which has vestibular edge 27, non-vestibular edge 28, intraoral surface 17 and cheek surface 19. During operation of retractor 10, intraoral surface 17 generally faces the patient's oral cavity and cheek surface 19 generally faces the patient's proximate inner cheek. Cheek retraction portion 16 is capable of retracting the entire cheek at once. Cheek retraction portion 16 according to this invention thus preferably includes a substantially flat fin-like configuration.

In terms of approximate dimensions of retractor 10 for most embodiments, cheek retraction portion 16 is preferably approximately 5 centimeters long and 1.5 centimeters wide. Lip retraction portion 14 is preferably approximately 4 centimeters long and approximately 2 centimeters wide. Handle portion 18 is preferably approximately 10 centimeters long and approximately 2 centimeters thick.

Handle portion 18 shown in FIG. 1 through FIG. 4 includes a transition region 25 and a manual region 20. Transition region 25 is adjacent to junction 21, and manual region 20 has extremity 29. As illustrated, manual region 20 has a substantially rectilinear shape and transition region 25 has a substantially flat shape.

For most embodiments of this invention, handle portion 18 is elongated and subtantially straight. Manual region 20 and transition region 25 can each have curvilinear and/or rectilinear aspects in form in accordance with this invention, so long as dexterity and function are furthered. In practicing this invention, handle portion 18 is preferably of such length, thickness and configuration as to facilitate manipulation by the dental practitioner.

Still referring to FIG. 1 through FIG. 4 and proceeding downward from extremity 13 along lip retraction portion 14 in a generally axial direction, retractor 10 bifurcates into two distinctly forked portions, viz., handle portion 18 and cheek retraction portion 16. When viewed from the perspectives shown in FIG. 3 and FIG. 4, outer edge 33 of transition region 20 is seen to derive from outer edge 12 of lip retraction portion 14, and vestibular edge 27 of cheek retraction portion 16 is seen to derive from inner edge 11 of lip retraction portion 14. When viewed from the perspectives shown in FIG. 1 and FIG. 2, inner edge 31 of transition region 25 is seen to to derive from non-vestibular edge 28 of cheek retraction portion 16.

Lip retraction portion 14 interfaces or merges with transition region 25 of handle portion 18 approximately at the location indicated by handle junction 21. Lip retraction portion 14 interfaces or merges with cheek retraction portion 16 approximately at the location indicated by retractor junction 23. Handle junction 21 (of lip retraction portion 14 and handle portion 18) is proximate and below (i.e., lower than) retractor junction 23 (of lip retraction portion 14 and cheek retraction portion 16). Handle junction 21 and retractor junction 23 do not represent distinct demarcations but rather represent less distinct transitional areas of retractor 10.

Description of the present invention is furthered by speaking in terms of various geometric relationships. For purposes of more clearly describing this invention, with some approximation each of portions 14, 16 and 18 may be envisioned to define therethrough its own imaginary longitudinal axis of symmetry. In addition, with some approximation each of portions 14 and 16 may be envisioned to define therethrough and to lie within its own imaginary longitudinal axial through plane of symmetry. For most embodiments of this invention, the axis defined by lip retraction portion 14 intersects or nearly intersects the axis defined by cheek retraction portion 16 as well as intersects or nearly intersects the axis defined by handle portion 18.

The axis defined by cheek retraction portion 16 approximately lies in the axially through plane defined by lip retraction portion 14. As shown in FIG. 1, the axis defined by lip retraction portion 14 approximately intersects the axis defined by cheek retraction portion 16 at obtuse angle Θ. For most embodiments obtuse angle Θ is preferably approximately one hundred (100) degrees. Also capable of envisaging is the approximate intersectional disposition of the axis defined by cheek retraction portion 16 at an acute angle with respect to the axis defined by handle portion 18.

Cheek retraction portion 16 projects from lip retraction portion 14 as a continuous extension which is disposed, in "semi-Mobius strip" fashion, in an approximately ninety (90) degree twist with respect to lip retraction portion 14. Concave side 22 of lip retraction portion 14 merges into cheek surface 19 of cheek retraction portion 16 and convex side 24 of lip retraction portion 14 merges into intraoral surface 17 of cheek retraction portion 16.

Transition region 25 is a more moderately twisted continuous extension of lip retraction portion 14. Concave side 22 of lip retraction portion 14 merges into first surface 36 of transition region 25 and convex side 24 of lip retraction portion 14 merges into second surface 38 of transition region 25.

As varyingly shown in FIG. 1 through FIG. 4, the axially through plane defined by lip retraction portion 14 is approximately perpendicular to the axially through plane defined by cheek retraction portion 16. Since the through plane defined by cheek retraction portion 16 is oriented in an approximately 90 degree rotational shift with respect to the through plane defined by lip retraction portion 14, it may be alternatively stated that the through plane defined by cheek retraction portion 16 approximately forms obtuse angle Θ with respect to the axis defined by lip retraction portion 14.

Figure 2:
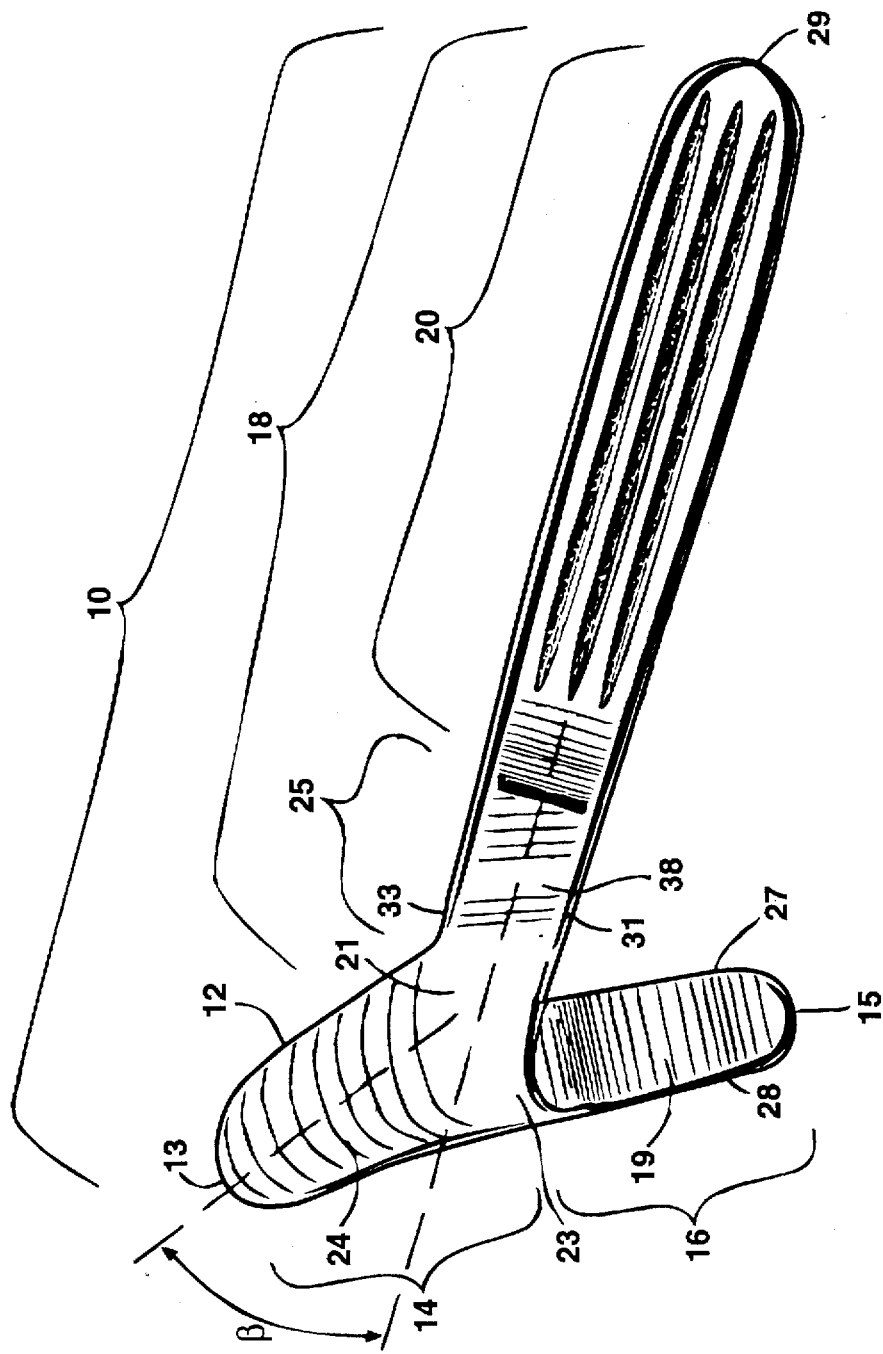
FIG. 2 is a perspective view of the retractor shown in FIG. 1, rotated approximately 90 degrees clockwise.

As shown in FIG. 2, in a first direction the axis defined by handle portion 18 approximately forms an acute angle with respect to the axis defined by lip retraction portion 14 (wherein concave side 22 approximately borders the angle inwardly) which is about equal to acute angle β. For most embodiments acute angle β is preferably approximately forty (40) degrees.

Figure 3:
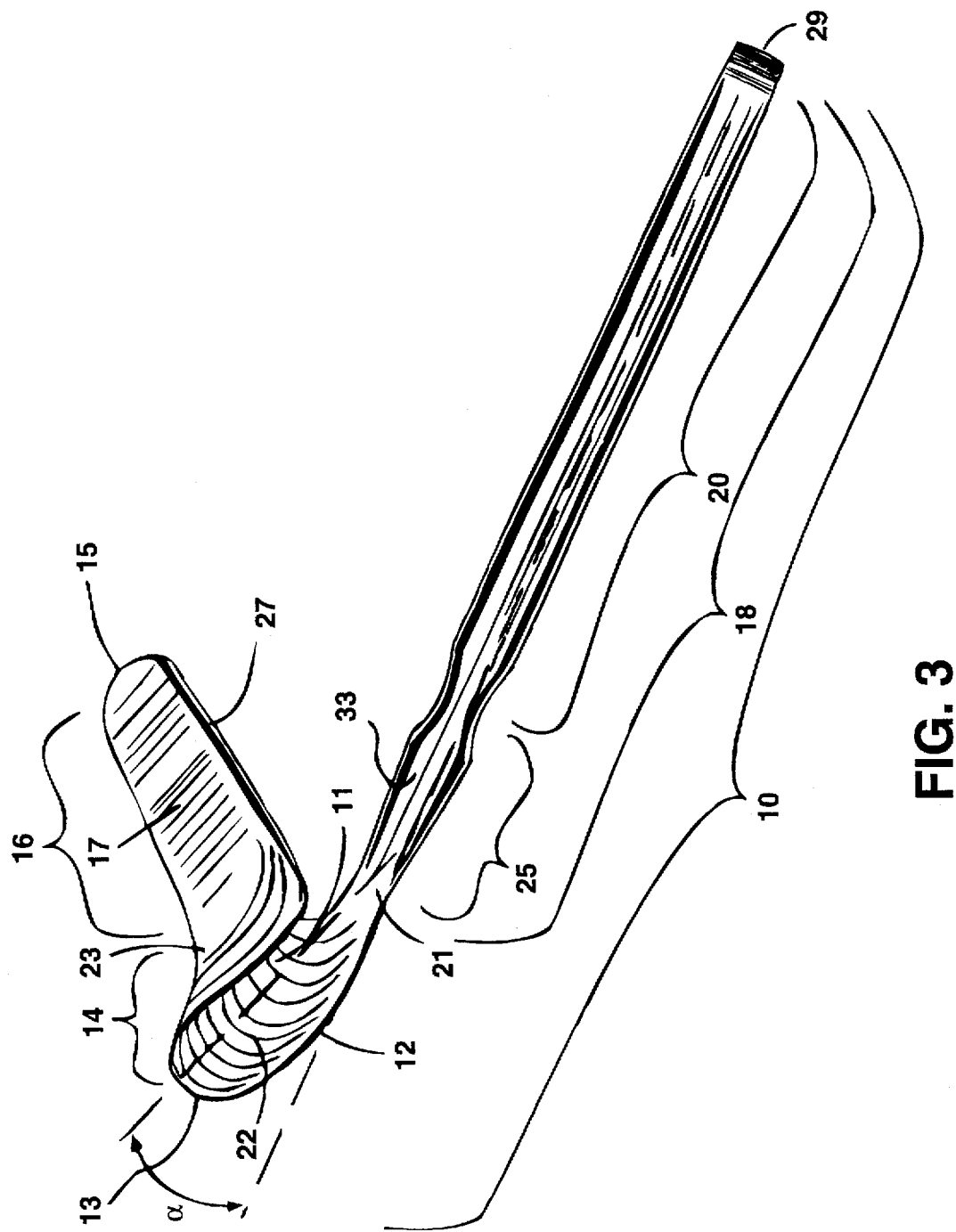
FIG. 3 is a perspective view of the retractor shown in FIG. 1, rotated approximately 180 degrees.

As shown in FIG. 3, in a second direction the axis defined by handle portion 18 approximately forms an acute angle with respect to the axis defined by lip retraction portion 14 (wherein outer edge 12 approximately borders the angle inwardly) which is about equal to acute angle α. For most embodiments acute angle α is preferably approximately twenty (20) degrees.

It is manifest from the figures that the axis defined by handle portion 18 and the axis defined by lip retraction portion 14 are obliquely oriented with respect to each other and may be considered to form a large obtuse angle therebetween. However, in furtherance of the instant description, it is more helpful to consider this obliqueness in terms of deviation of the respective axes from alignment with each other.

Since lip retraction portion 14 is retractor 10's crucial structure with regard to the positioning of retractor 10 in relation to the patient's mouth, a useful frame of reference is provided by the spatial system defined by the perpendicular intersection of (i) the axially through plane defined by lip retraction portion 14 and (ii) the axially normal plane defined by lip retraction portion 14. It is thus seen that the axis defined by handle portion 18 is acutely angled with respect to the axis defined by lip retraction portion 14 in two separate, perpendicular directions.

In other words, when lip retraction portion 14 is in place upon a patient's mouth in passive lip-cradling position, with some approximation lip retraction portion 14 may also be considered to be held horizontally in three dimensional Cartesian space so that handle junction 21 represents the origin and the axis defined by lip retraction portion 14 represents the "x axis" of the Cartesian coordinate system.

The "x-z" plane is the vertical plane through the "x axis" which is approximately tangential to the patient's face and which approximately corresponds with the axially normal plane defined by lip retraction portion 14. The "x-y" plane is the horizontal plane through the "x axis" which is approximately normal to the patient's face and which approximately corresponds with the axially through plane defined by lip retraction portion 14.

Hence, when retractor 10 is in passive mode, the axis defined by handle portion 18 is seen to diverge from the "x-z plane" by a first acute angle which is approximately equal to angle α; i.e., the vertical plane through the axis defined by handle portion 18 is seen to form angle α with respect to the "x-z plane." The axis defined by handle portion 18 is seen to diverge from the "x-y plane" by a second acute angle which is approximately equal to angle β; i.e., the horizontal plane through the axis defined by handle portion 18 is seen to form angle β with respect to the "x-y plane."

When lip retraction portion 14 is oriented with concave side 22 facing upward, retractor 10 is in position to be used in the upper left quadrant of the patient's mouth; when lip retraction portion 14 is oriented with concave side 22 facing downward, retractor 10 is in position to be used in the lower right quadrant of the patient's mouth.

Thus, when retractor 10 is passively in place in a patient's mouth, the orientation of handle portion 18 is such that handle portion 18 advantageously exits the mouth at an acute angle in each of two directions, up and back when on the upper dental arch and down and back when on the lower dental arch, so as to create a low profile with respect to the face of the patient. Given the range of manipulation of handle 18 in various directions by the dental professional who seeks to achieve desired exposure of the patient's oral cavity, it may be expected that handle 18 of retractor 10 when in activated mode will diverge from the "x-y" plane in an approximate range between 20 and 60 degrees and will diverge from the "x-z" plane in an approximate range between −20 and 60 degrees. Handle 18 will normally remain outside of the intraoral working area during activation, even when, as a consequence of the pliable nature of the patient's face, handle 18 diverges most extremely forward of the patient's face (i.e., typically on the order of minus twenty degrees with respect to the "x-y" plane).

Retractor 10 has curvature of the lip retraction portion in its axial direction, as best illustrated in FIG. 3. Retractor 10 features lip retraction portion 14 having moderate longitudinal curvature along the axis of lip retraction portion 14 and normal to the plane defined by lip retraction portion 14. Radially concave side 22 is longitudinally convex and radially convex side 24 is longitudinally concave.

Retractor 10 shown in FIG. 1 through FIG. 4 is to be used on the upper left area and the lower right area of the mouth. Lip retraction portion 14 of retractor 10 has tri-modal convexity/concavity, viz.: a first mode of convexity/concavity which is disposed in the axially radial direction in conformance with the lip form; a second mode of convexity/concavity which is disposed in the laterally planar direction in conformance with the arch form; and, a third mode of convexity/concavity which is disposed in the axially longitudinal direction. The third mode of convexity/concavity furthers vertical sway.

It is recalled that the axis defined by handle portion 18 forms an acute angle with respect to the "x-y plane" (the axially through plane defined by lip retraction portion 14) which is approximately represented by acute angle β in FIG. 2, and that acute angle β for most embodiments preferably equals approximately 40 degrees. It is also recalled that the range of manipulation of handle 18 by the dental practitioner when retractor 10 is in activated mode is such that handle 18 will diverge from the "x-y" plane in an approximate range between 20 and 60 degrees. The longitudinal convexity/concavity manifested by lip retraction portion 14 serves to facilitate this pivotable swing, approximately plus-or-minus 20 degrees up-or-down, which the dental practitioner will generally effectuate when activating retractor 10.

Figure 4:
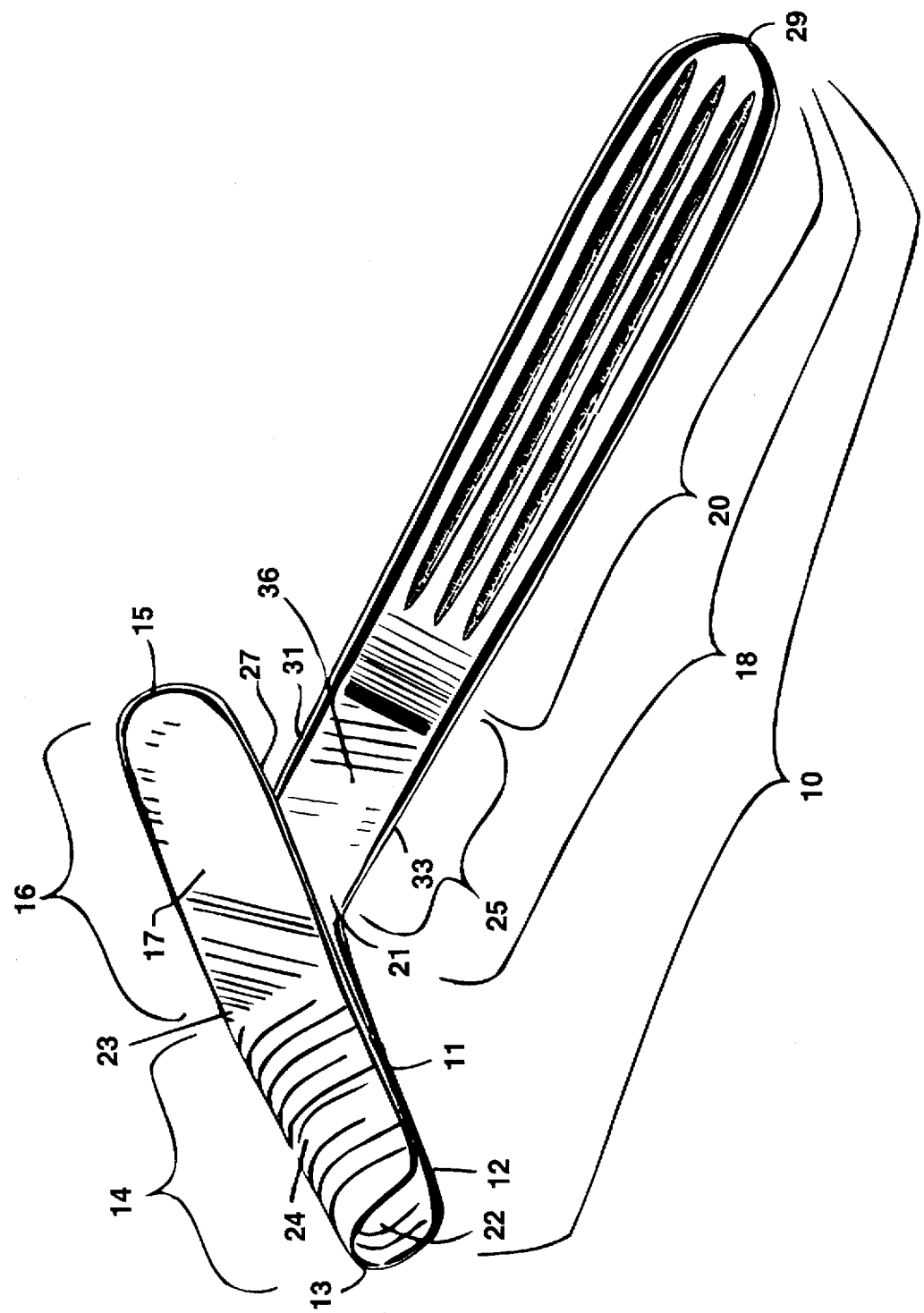
FIG. 4 is a perspective view of the retractor shown in FIG. 1, rotated approximately 90 degrees counterclockwise.

For some embodiments, as best illustrated in FIG. 4, slight longitudinal curvature along the axis of cheek retraction portion 16 and normal to the plane defined by cheek retraction portion 16 may be desirable. This uni-directional convexity/concavity (concavity of intraoral surface 17 and convexity of cheek surface 19) may afford moderate contouring with respect to the patient's inner cheek, thus promoting the patient's comfort during active cheek retraction when an extreme area of cheek surface 19 contacts the patient's inner cheek.

Figure 5:
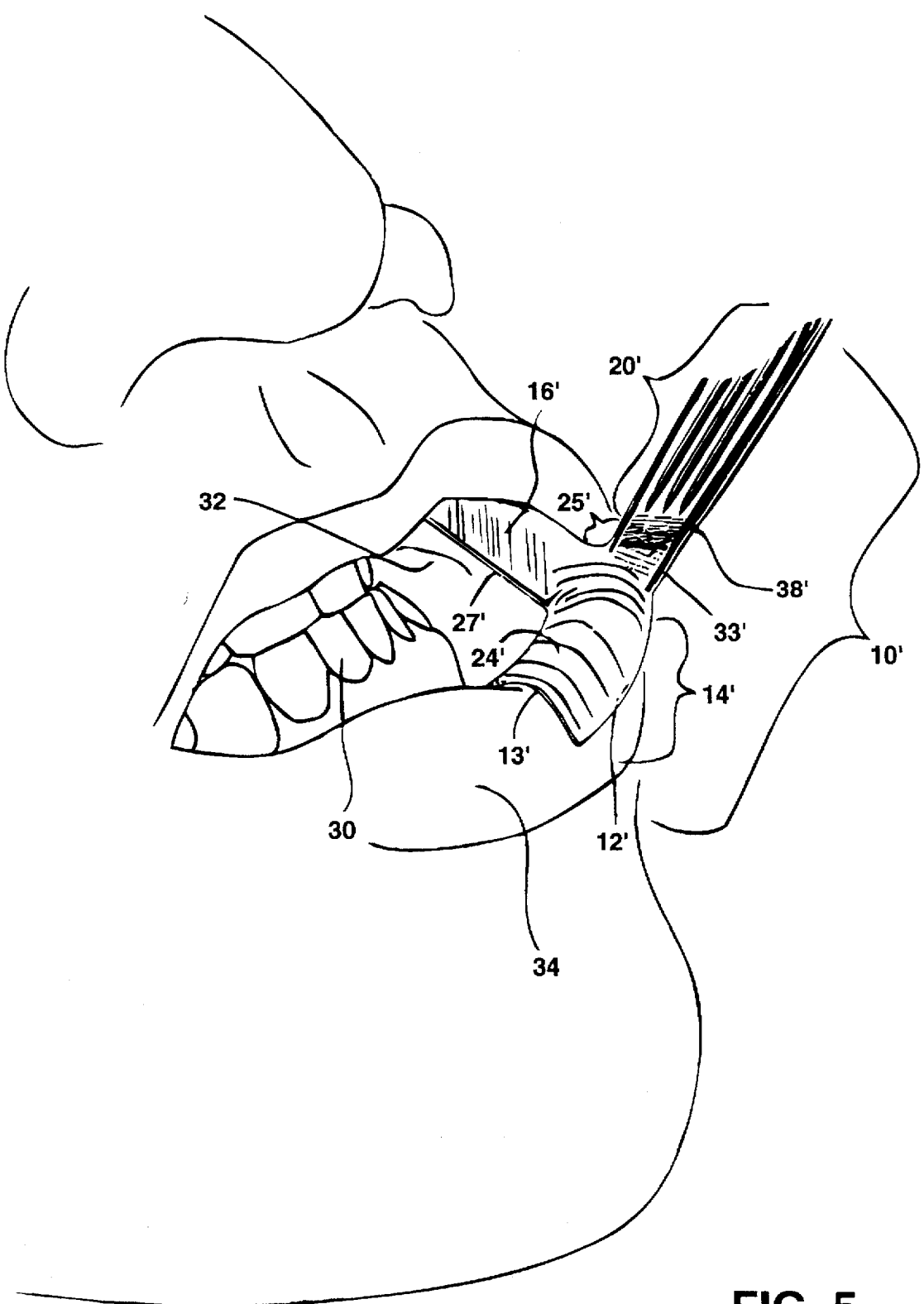
FIG. 5 is a perspective view of a "mirror image" embodiment of the retractor shown in FIG. 1, this embodiment intended for use in the lower left area or upper right area of a patient's mouth, this view illustrating use of this embodiment in the lower left quadrant of a patient's mouth.
Figure 6:
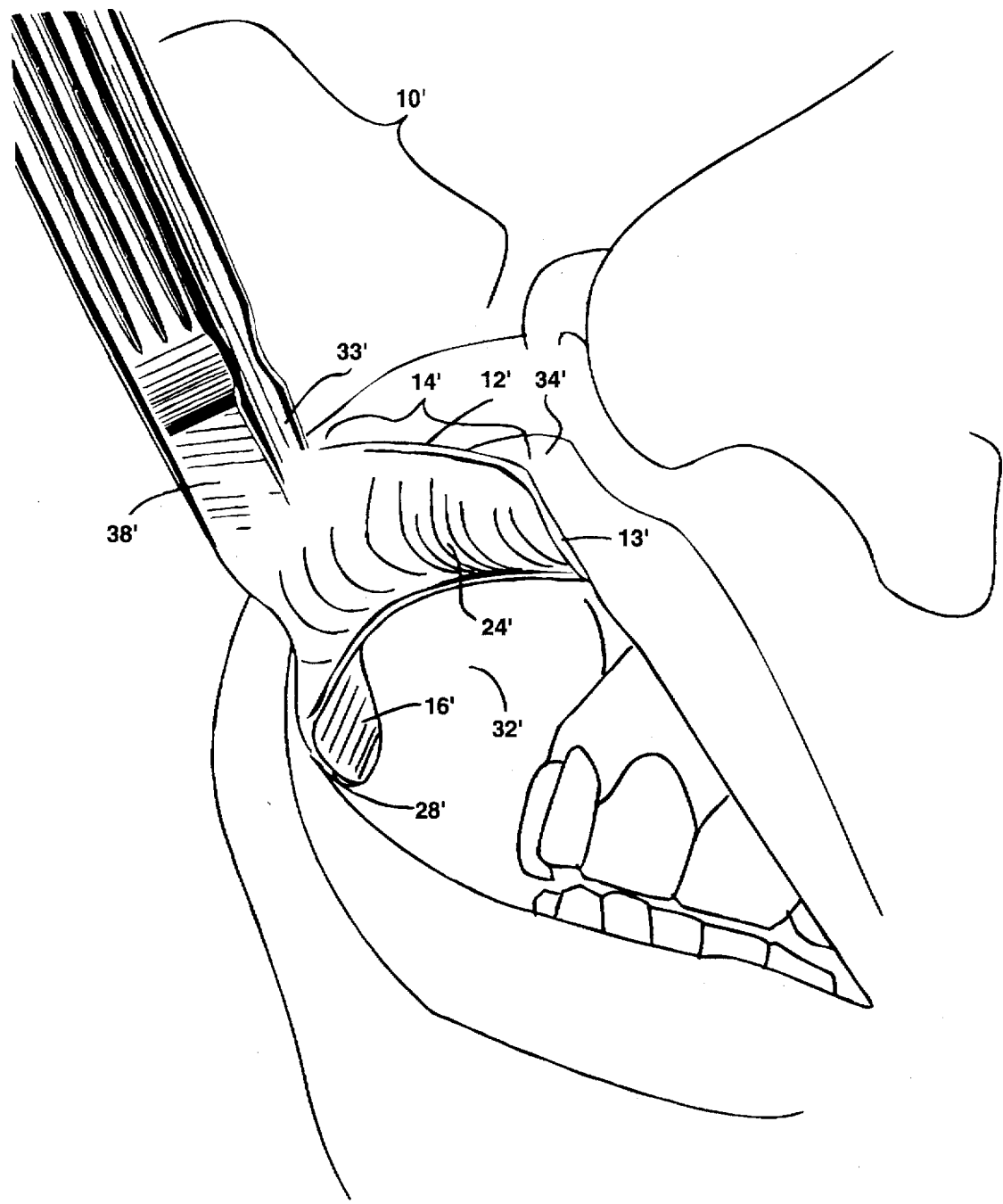
FIG. 6 is a perspective view of the retractor shown in FIG. 5, illustrating use in the upper right quadrant of a patient's mouth.
Figure 7:
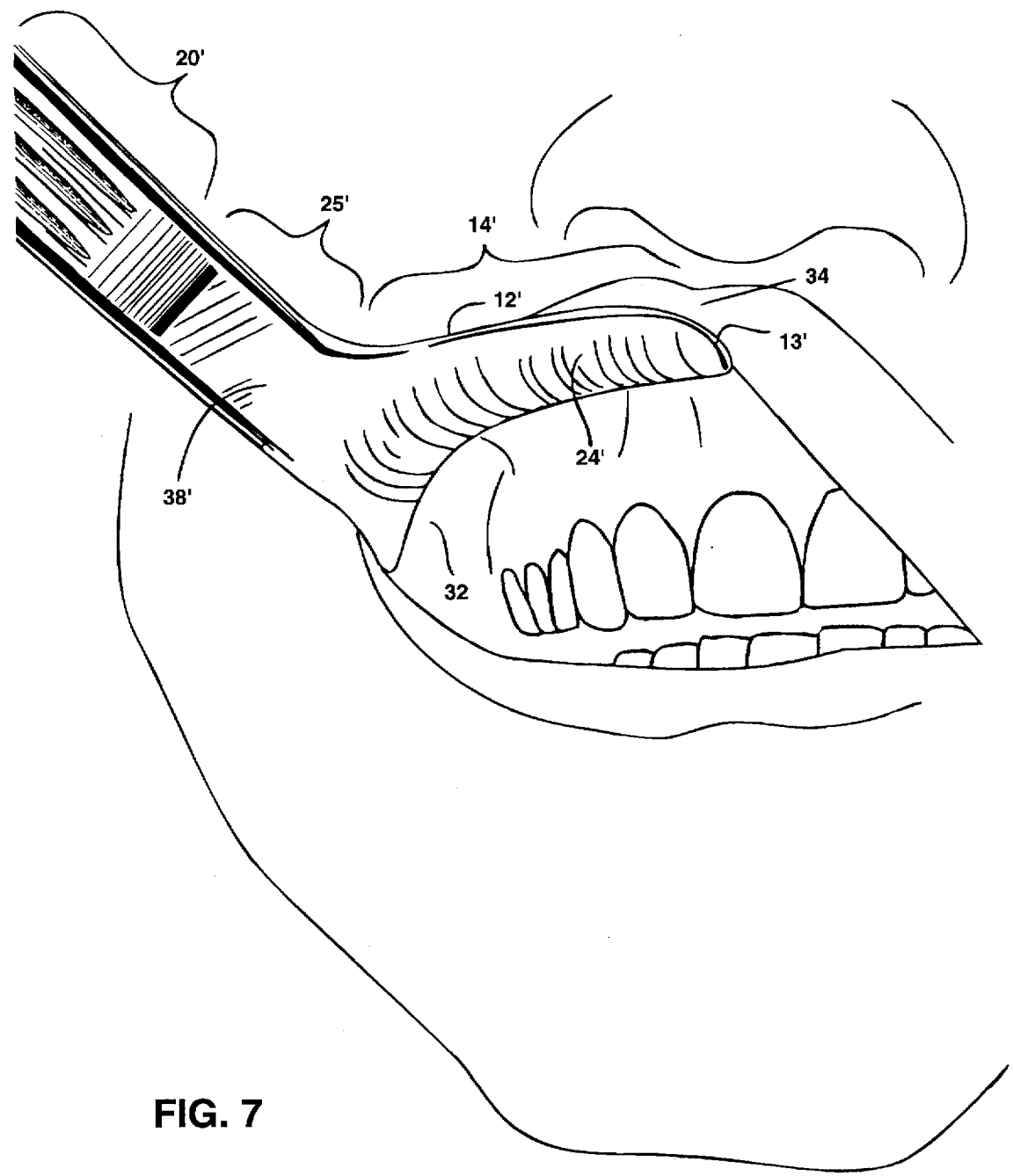
FIG. 7 is a perspective view of the retractor shown in FIG. 5, illustrating use in the upper right quadrant of a patient's mouth.

Most dental instruments include a "right-hand" version and a "left-hand" version for working in different sides of a patient's mouth. Retractor 10 shown in FIG. 1 through FIG. 4 is one version of the invention. Retractor 10' as shown in in FIG. 5 through FIG. 7 is an exact mirror image of retractor Retractor 10 shown in FIG. 1 through FIG. 4 would be used on the upper left and lower right areas of the mouth. Retractor 10' shown in FIG. 5 through FIG. 7 would be used on the upper right and lower left areas of the mouth. The reference numerals of FIG. 1 through FIG. 4 correspond to like features in FIG. 5 through FIG. 7, except that the features of FIG. 5 through FIG. 7 are designated with a "prime" (').

FIG. 5 shows retractor 10' in position in the lower left corner of patient's mouth 30. In FIG. 5, the cheek and lip are being retracted simultaneously by cheek retraction portion and lip retraction portion 14'. FIG. 6 shows retractor 10' simultaneously retracting lip 34 and cheek 32 in the upper right corner of a patient's mouth 30. Concave side 22' of lip retraction portion 14' receives patient's lip 34. FIG. 7 provides another view of retractor 10' in the upper right hand corner of patient's mouth 30. Lip retraction portion 14' (in particular, concave side 22') cradles the upper right hand portion of patient's lip 34 and cheek retraction portion 16' retracts patient's cheek 32.

Manual region 20 of handle portion 18/18' shown in FIG. 1 through FIG. 7 is substantially rectilinear, somewhat curvilinear and rather flat in shape. For some embodiments of this invention substantial rectilinearity of handle portion 18 may be preferred as affording the practitioner a surer grip. Surface features such as corrugations 40 of manual region 20, shown in FIG. 2 and FIG. 4 through FIG. 7, may also serve to further dexterity. The ordinarily skilled artisan will recognize that a variety of shapes and surfaces of the inventive retractor's handle are feasible for practicing the inventive retractor, the main consideration being that the handle sufficently advance the practitioner's manual adroitness as to fully realize the efficacy of the inventive retractor.

For example, although not shown, manual region 20 can be envisioned to be moderately tapered toward extremity 29, a feature which may also promote manipulative skill for some embodiments. Also, manual region 20 of handle portion 18/18' shown in the figures has four sides defining a geometric cross-section which is generally rectangular. For some embodiments the geometric cross-section is preferably appreciably trapezoidal so that the practitioner's thumb may be advantageously placed on an inclined side of manual region 20 in furtherance of the practitioner's dexterity.

With reference to the figures in general, the two retractive structures of retractor 10/10' (i.e., lip retraction portion 14/14' and cheek retraction portion 16/16') and the handle structure (i.e., handle portion 18/18') represent three distinct inventive features which synergistically afford the dental practitioner the capability of exposing an entire quadrant of the patient's oral area by retracting both the lip and cheek simultaneously or each individually. The inventive retractor is essentially two retractors in one.

Other advantages are afforded by the configuration of retractor 10/10' in terms of both its angularities and curvatures. Retractor 10/10' has a natural arch-like shape. Either lip retraction portion 14/14' or cheek retraction portion 16/16' can be activated to retract only those areas requiring visualization while allowing passive placement of the other portion. This process is accomplished with a simple change in the rotation of handle portion 18/18'.

Handle portion 18/18' permits skillful manipulation by the dental surgeon or surgical assistant who seeks to work on specific areas at particular points in time; exposure of these specific areas can be accomplished with great precision. To the exact degree required for the lip and/or the cheek, retraction is performed of: (i) the lip only; or, (ii) the cheek only; or, (iii) the lip and the cheek together.

During passivity handle portion 18/18' exits the mouth and projects, like a vector which points in the general direction of manual retraction, at acute angles up and back (when on the upper dental arch) or down and back (when on the lower dental arch), thus allowing handle portion 18/18' to maintain a low profile against the patient's face; hence, in all modes of activity and passivity, the instrument and practitioner's hand are conveniently and expediently situated outside the critical peri-oral working region.

Moreover, a common complaint concomitant with dental surgery is pressure necrosis of the patient's tissues, which is caused by an instrument leaning against tissues for extended periods of time without allowing blood circulation to the area. While grasping handle portion 18/18' with lip retraction portion 14/14' cradling the patient's lip, the dental professional will be enabled to periodically relax lip retraction portion 14/14' and/or cheek retraction portion 16/16'. The opportunity for such periodic relaxation which the inventive retractor affords should virtually eliminate the potential for pressure necrosis of the tissues. Retractor 10/10' is intrinsically prevented from pinching the lip of the patient whether retractor 10/10' is actively retracting or resting passively in the mouth.

Handle portion 18/18' conjoins with the working portion of retractor 10/10' at handle junction 21/21' (of lip retraction portion 14/14' and handle portion 18/18'), which is a short but significant distance from retractor junction 23/23' (of lip retraction portion 14/14' and cheek retraction portion 16/16'). Transition region 25/25' of handle portion 18/18' is interposed between handle junction 21/21' and manual region 20/20'. Transition region 25/25' has a first surface 36/36' which springs from the outer edge 12/12' region of concave side 22/22' so as to be nonhindering of the patient's lip when retractor 10/10' is in position. Also, transition region 25/25' is of such extent as to sufficiently distance lip retraction portion 14/14' and manual portion 20/20', thereby preventing the dimensionally thicker manual portion 20/20' from interfering with the patient's lip.

While the invention has been disclosed with reference to certain described embodiments, numerous changes, alterations and modifications to the described embodiments are possible without departing from the spirit and scope of the invention, as defined in the appended claims and equivalents thereof.

What is claimed is:

1. A dental device, comprising:

a substantially straight body for manipulation;

a substantially furrowed arm for lip retraction, said arm having at opposite sides a substantially concave surface and a substantially convex surface, said arm branching off said body, from an end of said body, at an acute orientation with respect to said body in each of two perpendicular directions; and a substantially flat finger for cheek retraction, said finger having at opposite sides a pair of substantially planar surfaces, said finger branching off said arm, from a location of said arm which is near said end of said body, at an acute orientation with respect to said body and an obtuse orientation with respect to said arm, said finger being a continuous extension of said arm wherein said substantially concave surface merges into one said substantially planar surface and said substantially convex surface merges into the other said substantially planar surface, said finger being disposed in an approximately ninety degree twist with respect to said arm.

2. A dental instrument, comprising:

a substantially curvilinearly-channeled structure for retracting a lip;

a substantially flat structure for retracting a cheek; and a substantially linear structure for manipulating said instrument;

said substantially curvilinearly-channeled structure being connected to said substantially flat structure and said substantially straight structure at proximate locations;

said substantially curvilinearly-channeled structure and said substantially flat structure approximately defining intersecting axes which form an obtuse angle;

said substantially curvilinearly-channeled structure and said substantially linear structure approximately defining intersecting axes which form an acute angle in each of two perpendicular directions.

3. An apparatus for manipulatively retracting a subject's lip and/or cheek, comprising:

a lip retraction member which is substantially curved-trough-shaped;

a cheek retraction member which is substantially flat-fin-shaped; and a handle member which is elongated and substantially straight;

said lip retraction member approximately defining a first longitudinal axis, a first imaginary plane and a second imaginary plane, said first imaginary plane being through said first longitudinal axis and through said lip retraction member, said second imaginary plane being through said first longitudinal axis and perpendicular to said first imaginary plane, said lip retraction member having a first extremity and a second extremity;

said cheek retraction member approximately defining a second longitudinal axis, said cheek retraction member having a third extremity and a fourth extremity;

said handle member approximately defining a third longitudinal axis, said handle member having a fifth extremity and a sixth extremity;

said first extremity joining said third extremity at a first junction whereby said first longitudinal axis and said second longitudinal axis approximately intersect at said first junction so as to form an obtuse angle;

said first extremity joining said fifth extremity at a second junction which is proximate said first junction and nearer than said first junction to said sixth extremity, whereby said first imaginary plane and said third longitudinal axis approximately intersect at said second junction so as to form a first acute angle, and whereby said second imaginary plane and said third longitudinal axis approximately intersect so as to form a second acute angle.

4. An apparatus for retracting as in claim 3, wherein said lip retraction member twistingly and continuously merges into said cheek retraction member at said first junction.

5. An apparatus for retracting as in claim 3, wherein:

said lip retraction member has a first lateral edge and a second lateral edge;

said first junction is located in the vicinity of said first lateral edge; and said second junction is located in the vicinity of said second lateral edge.

6. An apparatus for retracting as in claim 5, wherein said lip retraction member has curvature of said first lateral edge and said second lateral edge.

7. An apparatus for retracting as in claim 3, wherein said lip retraction member has curvature in the direction of said first longitudinal axis.

8. An apparatus for retracting as in claim 3, wherein said cheek retraction member has curvature in the direction of said second longitudinal axis.

9. An apparatus for retracting as in claim 3, wherein said obtuse angle approximately equals 100 degrees.

10. An apparatus for retracting as in claim 3, wherein said first acute angle approximately equals 40 degrees.

11. An apparatus for retracting as in claim 3, wherein said second acute angle approximately equals 20 degrees.

12. An apparatus for retracting as in claim 3, wherein said device is made of at least one material selected from the group consisting of steel, plastic, rubber and composite.

13. An apparatus for retracting as in claim 3, wherein said device comprises a solid piece, said solid piece comprising said lip retraction member, said cheek retraction member and said handle member.

14. An apparatus for retracting as in claim 3, wherein said device comprises a first solid piece and a second solid piece, said first solid piece comprising said lip retraction member and said cheek retraction member, said second solid piece comprising said handle member.

15. An apparatus for retracting as in claim 3, wherein said lip retraction member is approximately 4 centimeters long and 2 centimeters wide.

16. An apparatus for retracting as in claim 3, wherein said cheek retraction member is approximately 5 centimeters long and 1.5 centimeters wide.

17. An apparatus for retracting as in claim 3, wherein said handle member is approximately 10 centimeters long and 2 centimeters thick.

18. An apparatus for retracting as in claim 3, wherein said handle member has a shape which is characterized by substantial curvilinearity.

19. An apparatus for retracting as in claim 3, wherein said handle member has a shape which is characterized by substantial rectilinearity.

20. An apparatus for retracting as in claim 3, wherein said cheek retraction member approximately defines a third imaginary plane, said third imaginary plane being through said second longitudinal axis and through said cheek retraction member, said first extremity joining said third extremity at said first junction whereby said first imaginary plane and said third imaginary plane are approximately perpendicular.

\* \* \* \* \*